(12) United States Patent
Inoue

(10) Patent No.: US 9,221,052 B2
(45) Date of Patent: Dec. 29, 2015

(54) DISPENSING DEVICE

(71) Applicant: Panasonic Healthcare Holdings Co., Ltd., Tokyo (JP)

(72) Inventor: Takahiro Inoue, Kyoto (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 34 days.

(21) Appl. No.: 14/166,468

(22) Filed: Jan. 28, 2014

(65) Prior Publication Data

US 2014/0138405 A1 May 22, 2014

Related U.S. Application Data

(63) Continuation of application No. PCT/JP2012/080645, filed on Nov. 27, 2012.

(30) Foreign Application Priority Data

Dec. 22, 2011 (JP) .................................. 2011-281113

(51) Int. Cl.
  *G06F 17/00* (2006.01)
  *B01L 3/00* (2006.01)
  (Continued)

(52) U.S. Cl.
  CPC .................. *B01L 3/52* (2013.01); *B01L 3/0227* (2013.01); *C12M 29/00* (2013.01); *B01L 2200/146* (2013.01); *B01L 2400/0487* (2013.01); *B01L 2400/06* (2013.01); *G01N 35/1016* (2013.01)

(58) Field of Classification Search
  CPC . B01L 3/52; B01L 2400/0487; B01L 3/0227; B01L 2200/146; B01L 2400/06; G01N 35/1016; C12M 29/00

USPC .............................................. 222/55; 425/146
  See application file for complete search history.

(56) References Cited

U.S. PATENT DOCUMENTS 4,989,756 A * 2/1991 Kagamihara et al. ............ 222/55
5,199,607 A * 4/1993 Shimano .......................... 222/55
(Continued)

FOREIGN PATENT DOCUMENTS

JP         H4-3266 B2     3/1988
JP         2009-291103 A   12/2009
(Continued)

OTHER PUBLICATIONS

International Search Report PCT/JP2012/080645 dated Feb. 12, 2013 with English translation.

*Primary Examiner* — Patrick M Buechner
*Assistant Examiner* — Jeremy W Carroll
(74) *Attorney, Agent, or Firm* — McDermott Will & Emery LLP

(57) ABSTRACT

A dispensing device includes: a syringe; a first pump; a second pump; a first flowmeter; and a first control unit configured to correct a plurality of initial driving voltages for the first pump by calculating a first ratio of, with respect to a driving voltage for the first pump associated in advance with a target flow rate in a case where the syringe draws in a first fluid as the fluid, a driving voltage for the first pump when the first flowmeter measures a flow rate corresponding to the target flow rate in a case where the syringe draws in the first fluid, and multiplying, by the first ratio, the plurality of initial driving voltages for the first pump respectively associated in advance with a plurality of target flow rates in a case where the syringe draws in a second fluid as the fluid.

6 Claims, 11 Drawing Sheets

(51) Int. Cl.
*C12M 1/00* (2006.01)
*B01L 3/02* (2006.01)
*G01N 35/10* (2006.01)

(56) References Cited

U.S. PATENT DOCUMENTS 5,332,125 A * 7/1994 Schmitkons et al. ............. 222/1
5,730,323 A * 3/1998 Osborne ........................ 222/55
5,992,686 A * 11/1999 Cline et al. ....................... 222/1
7,963,422 B2 * 6/2011 Ramnarine ....................... 222/1
2005/0035143 A1 * 2/2005 Massaro et al. .................. 222/1

FOREIGN PATENT DOCUMENTS

WO  2007/148686 A1  12/2007
WO  2010/110265 A1  9/2010

* cited by examiner

INITIAL MANIPULATED VARIABLE WITH RESPECT TO FIRST
TARGET FLOW RATE WHEN DRAWING IN LIQUID (PUMP P1)

T1

| FIRST TARGET FLOW RATE (ml/s) | F1 | F2 | F3 |
|---|---|---|---|
| INITIAL MANIPULATED VARIABLE (V) | G11 | G12 | G13 |

FIG. 5

INITIAL MANIPULATED VARIABLE WITH RESPECT TO FIRST
TARGET FLOW RATE WHEN DRAWING IN AIR (PUMP P1)

T2

| FIRST TARGET FLOW RATE (ml/s) | F1 | F2 | F3 |
|---|---|---|---|
| INITIAL MANIPULATED VARIABLE (V) | G21 | G22 | G23 |

FIG. 6

CORRECTED INITIAL MANIPULATED VARIABLE WITH RESPECT TO
FIRST TARGET FLOW RATE WHEN DRAWING IN LIQUID (PUMP P1)

T3

| FIRST TARGET FLOW RATE (ml/s) | F1 | F2 | F3 |
|---|---|---|---|
| CORRECTED INITIAL MANIPULATED VARIABLE (V) | G11 X K1 | G12 X K1 | G13 X K1 |

FIG. 7

INITIAL MANIPULATED VARIABLE WITH RESPECT TO SECOND
TARGET FLOW RATE WHEN DISCHARGING LIQUID (PUMP P2)

INITIAL MANIPULATED VARIABLE WITH RESPECT TO SECOND
TARGET FLOW RATE WHEN DISCHARGING AIR (PUMP P2)

CORRECTED INITIAL MANIPULATED VARIABLE WITH RESPECT TO
SECOND TARGET FLOW RATE WHEN DISCHARGING LIQUID (PUMP P2)

DISPENSING DEVICE

CROSS-REFERENCE TO RELATED APPLICATIONS

This is a continuation application of International Patent Application No. PCT/JP2012/080645 filed Nov. 27, 2012, which claims the benefit of priority to Japanese Patent Application No. 2011-281113 filed Dec. 22, 2011. The full contents of the International Patent Application are incorporated herein by reference.

BACKGROUND OF THE INVENTION

1. Field of the Invention

The present disclosure relates to a dispensing device.

2. Description of the Related Art

For example, Japanese Patent Application Publication No. 2009-291103 discloses a dispensing device configured to discharge to a culture container liquid such as a culture medium for culturing a cell and drawing in the liquid contained in the culture container.

The dispensing device of Japanese Patent Application Publication No. 2009-291103, for example, draws liquid into a syringe and discharges the liquid in the syringe, using pressure generated by a pump. For example, when drawing in or discharging a liquid, a driving voltage associated in advance with a target flow rate of a liquid is supplied to a pump so that the liquid will be passed at the target flow rate. However, for example, in the case where the pump has deteriorated with time and/or a warm-up operation being a low load operation of the pump has not been performed for a predetermined time period, the flow rate of the liquid may vary although a driving voltage associated in advance with the target flow rate of the liquid is supplied to the pump. Further, for example, a paint discharge rate control device of Japanese Examined Patent Application Publication No. 4-3266 determines when discharging paint from a nozzle, a correction value for fixing the flow rate of the paint subsequently discharged to the target flow rate based on the mean value of the flow rates measured by a flowmeter during a predetermined time period. However, this paint discharge rate control device, for example, is not capable of determining a plurality of correction values corresponding to a plurality of target flow rates by a single determination of the correction value. Thus, even if a dispensing device draws in or discharges a liquid, for example, with the technique of Japanese Examined Patent Application Publication No. 4-3266 applied thereto, for example, the flow rate of the liquid cannot reach the target flow rate in the case where the target flow rate is changed in each suction or discharge, which results in varying the flow rate of the liquid. Thus, for example, liquid may adhere to the filter provided between the syringe and the pump, due to the varying flow rate when drawing the liquid into the syringe. Further, the liquid may splatter around the dish for the dispensed liquid and contaminate the surroundings, due to the varying flow rate of the liquid discharged from the syringe. Further, for example, there may be difficulty in keeping constant the working time taken to repeat drawing and discharging a predetermined volume of liquid for a predetermined number of times.

SUMMARY OF THE INVENTION

A dispensing device according to an aspect of the present disclosure, includes: a syringe configured to draw in or discharge a fluid; a first pump configured to generate a pressure to draw the fluid into the syringe; a second pump configured to generate a pressure to discharge the fluid in the syringe; a first flowmeter disposed on a first flow path between the syringe and the first pump; and a first control unit configured to correct a plurality of initial driving voltages for the first pump by calculating a first ratio of, with respect to a driving voltage for the first pump associated in advance with a target flow rate in a case where the syringe draws in a first fluid as the fluid, a driving voltage for the first pump when the first flowmeter measures a flow rate corresponding to the target flow rate in a case where the syringe draws in the first fluid, and multiplying, by the first ratio, the plurality of initial driving voltages for the first pump respectively associated in advance with a plurality of target flow rates in a case where the syringe draws in a second fluid as the fluid.

Other features of the present disclosure will become apparent from descriptions of the present specification and of the accompanying drawings.

BRIEF DESCRIPTION OF THE DRAWINGS

For more thorough understanding of the present disclosure and advantages thereof, the following description should be read in conjunction with the accompanying drawings, in which:

FIG. 5 is a diagram illustrating an initial manipulated variable of a first pump with respect to a first target flow rate when drawing in liquid, in an embodiment of the present disclosure;

FIG. 6 is a diagram illustrating an initial manipulated variable of a first pump with respect to a first target flow rate when drawing in air, in an embodiment of the present disclosure;

FIG. 7 is a diagram illustrating a corrected initial manipulated variable of a first pump with respect to a first target flow rate when drawing in liquid, in an embodiment of the present disclosure;

DETAILED DESCRIPTION OF THE INVENTION

At least the following details will become apparent from descriptions of the present specification and of the accompanying drawings.

—Dispensing Device—

Figure 1:
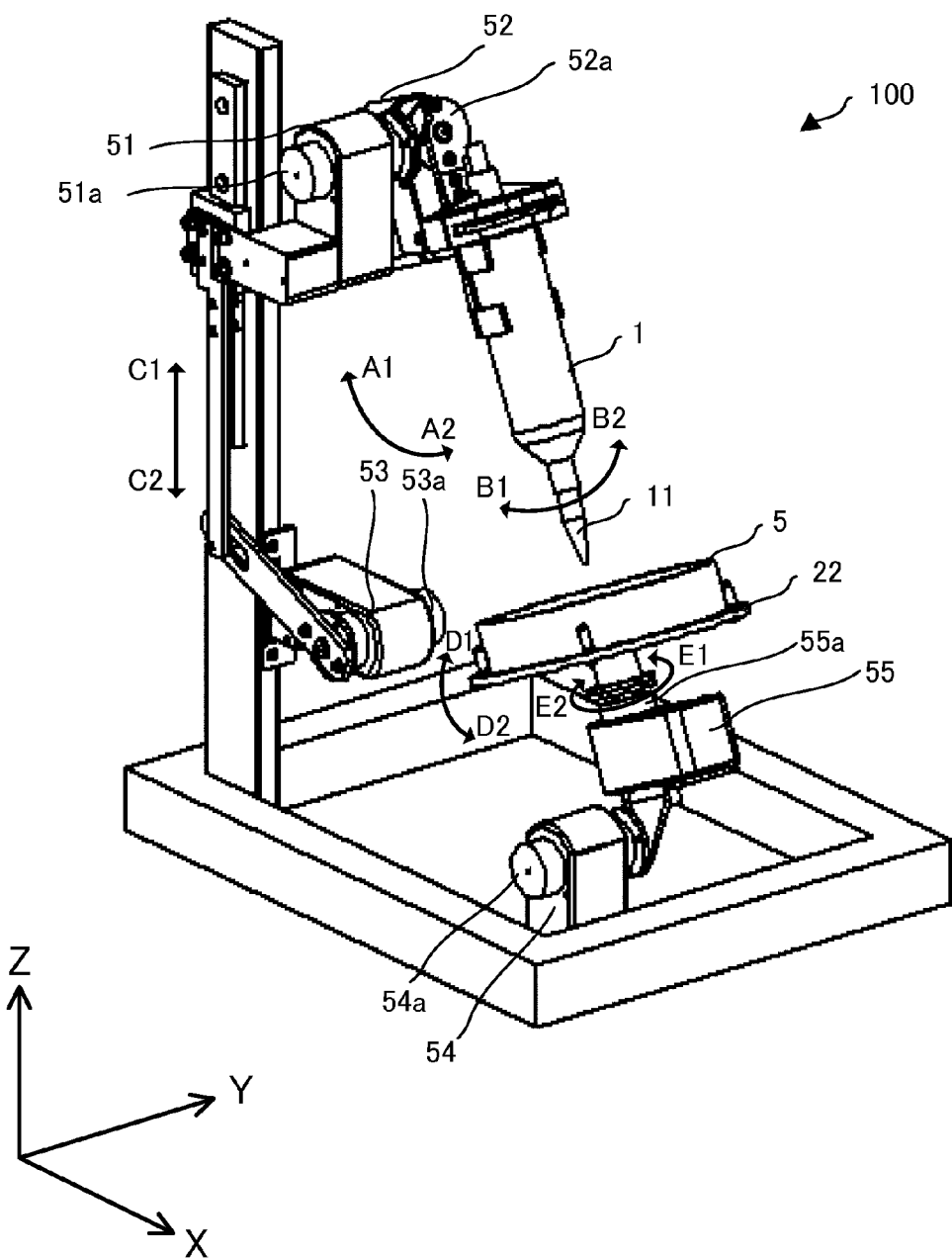
FIG. 1 is a perspective view illustrating a configuration of a dispensing device according to an embodiment of the present disclosure.

Hereinafter, description will be given of a dispensing device according to according to an embodiment of the present disclosure with reference to FIG. 1. FIG. 1 is a perspective view illustrating a configuration of the dispensing device according to an embodiment of the present disclosure.

A dispensing device 100 is a device for drawing in or discharging a liquid (fluid) such as a culture medium for culturing a cell and the like. Note that a configuration in which the dispensing device 100 draws in or discharges liquid will be described later. The dispensing device 100 includes a syringe 1, servo motors 51 to 55, and a dish mounting portion 22.

The syringe 1 includes a nozzle 11 to draw liquid into the syringe 1 or discharging liquid inside the syringe 1.

The dish 5 is mounted on the dish mounting portion 22 such that the dish 5 is disposed below (in the negative Z-axis direction) the syringe 1. Note that the dish 5 is a case, for example, made of resin, in which a liquid such as a culture medium for culturing a cell and the like is stored.

The servo motors 51 to 53 are motors to control the position and the posture of the syringe 1. The servo motors 54 and 55 are motors to control the position, posture, and rotation of the dish mounting portion 22. The servo motor 51 drives the syringe 1 in the A1 direction or the A2 direction about a drive axis 51a parallel to the Y-axis. The servomotor 52 drives the syringe 1, in the B1 direction or the B2 direction about the drive axis 52a perpendicular to the plane defined by the Y-axis and the syringe 1. The servo motor 53 drives the syringe 1 in an up and down direction (C1 direction or C2 direction, Z-axis direction). The servomotor 54 drives the dish mounting portion 22 in the D1 direction or the D2 direction about the drive axis 54a parallel to the Y-axis. The servomotor 55 rotates the dish mounting portion 22 in the E1 direction or the E2 direction about the drive axis 55a perpendicular to the plane of the dish mounting portion 22 on which the dish 5 is to be mounted.

—Configuration for Drawing in or Discharging Liquid—

Figure 2:
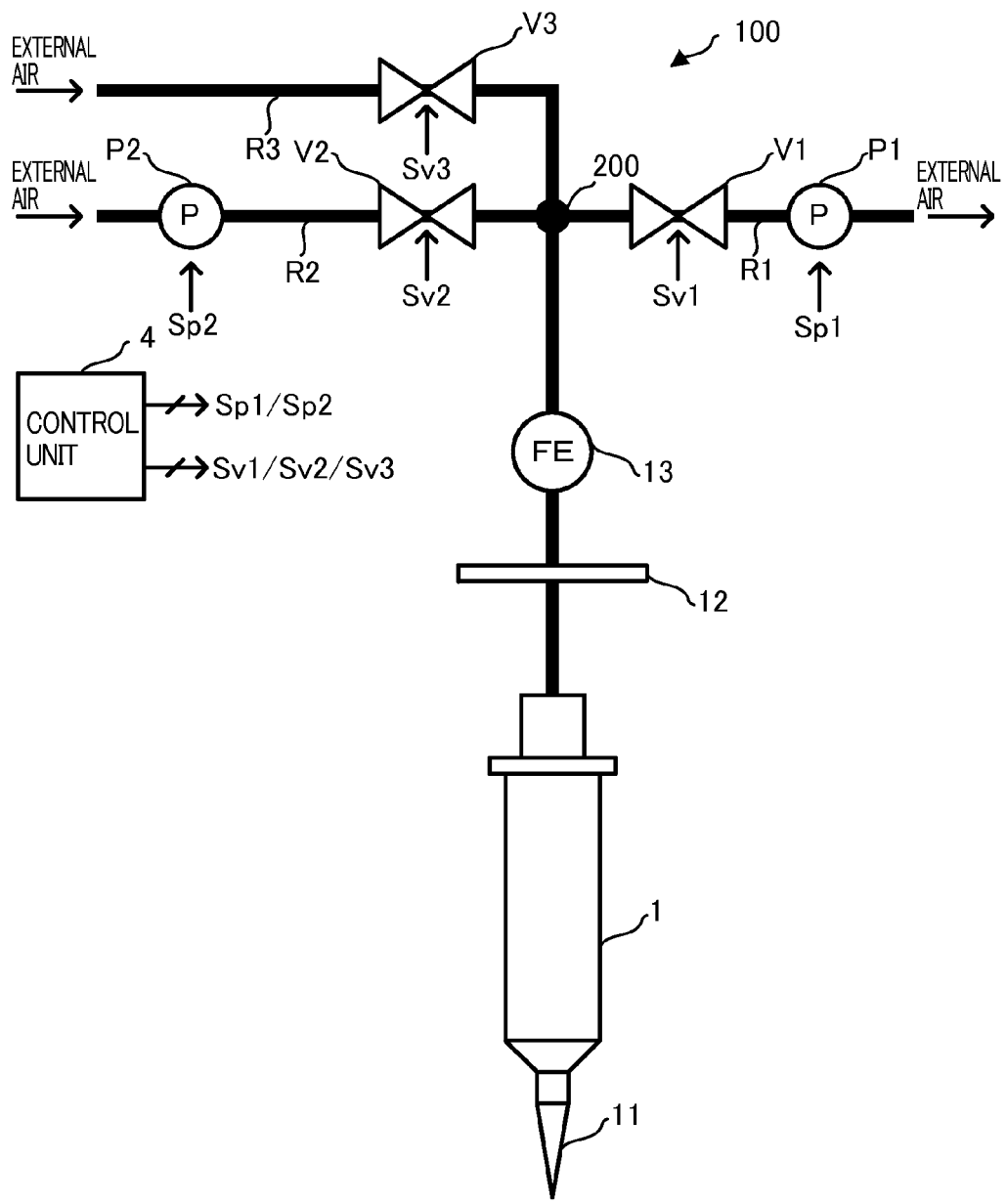
FIG. 2 is a block diagram illustrating a configuration in which a dispensing device draws in or discharges a liquid, according to an embodiment of the present disclosure.

Hereinafter, a description will be given of a configuration in which the dispensing device according to an embodiment of the present disclosure draws in or discharges a liquid, with reference to FIG. 2. FIG. 2 is a block diagram illustrating a configuration in which the dispensing device draws in or discharges a liquid, according to an embodiment of the present disclosure.

The dispensing device 100 includes the aforementioned syringe 1, a control unit 4 (first control unit, second control unit, first discrimination unit, second discrimination unit, first output unit, second output unit), a filter 12, a flow rate sensor 13 (first flowmeter, second flowmeter), a pump P1 (first pump), a pump P2 (second pump), and valves V1, V2 and V3.

The pumps P1 and P2 are, for example, diaphragm pumps that generate pressures corresponding to driving voltages supplied to the pumps P1 and P2. The pump P1 is a suction pump that discharges gas inside the syringe 1 through a first flow path R1, and generates a pressure for drawing the liquid into the syringe 1 through the nozzle 11. The pump P2 is a discharge pump that takes the external air (gas) into the syringe 1 through a second flow path R2, and generates pressure for discharging the liquid inside the syringe 1 through the nozzle 11.

The valve V1 is connected in such a manner as to open/close a section of the first flow path R1 between the syringe 1 and the pump P1. The valve V2 is connected in such a manner as to open/close a section of the second flow path R2 between the syringe 1 and the pump P2. The valve V3 is connected in such a manner as to open/close a section of the third flow path between the syringe 1 and the other end opposite to the one end connected to the syringe 1. Note that, for example, a solenoid valve, an electric pinch valve, or the like, which is controllable with a control signal, can be used for the valves V1 to V3.

The first flow path R1, the second flow path R2, and the third flow path R3 join and branch at a single merging-and-diverting point 200. That is, respective parts of the first flow path R1, the second flow path R2, and the third flow path R3 join on the syringe 1 side, resulting in forming a path common to the first flow path R1, the second flow path R2, and the third flow path R3. The filter 12 such as a membrane filter is inserted into a section between the syringe 1 and the merging-and-diverting point 200 that is a part of the flow path common to the first flow path R1, the second flow path R2, and the third flow path R3, in order to prevent contamination of the liquid in the syringe 1 which would be caused by unwanted bacteria mixing therein.

The flow rate sensor 13 is a sensor that detects a flow rate (hereinafter, referred to as "first flow rate") of the air when the air in the syringe 1 is discharged through the first flow path R1 by the pressure generated by the pump P1, and a flow rate (hereinafter, referred to as "second flow rate") of the air when air is taken into the syringe 1 through the second flow path R2 by the pressure generated by the pump P2, and outputs a signal indicative of a detection result. The flow rate sensor 13 is disposed on the part of the flow path shared by the first flow path R1, the second flow path R2, and the third flow path R3, in a manner to be used in common by all the paths. Note that a configuration for measuring the first and second flow rates using the flow rate sensor 13 will be described later.

The control unit 4 controls the servo motors 51 to 55, the valves V1 to V3, and the pumps P1 and P2. The control unit 4 outputs control signals Sv1 to Sv3 for controlling the valves V1 to V3. The control unit 4 outputs the control signals Sp1 and Sp2 for controlling the pumps P1 and P2. Note that the details of the control unit 4 will be described later.

—Main Circuit and Interface Circuit—

Figure 3:
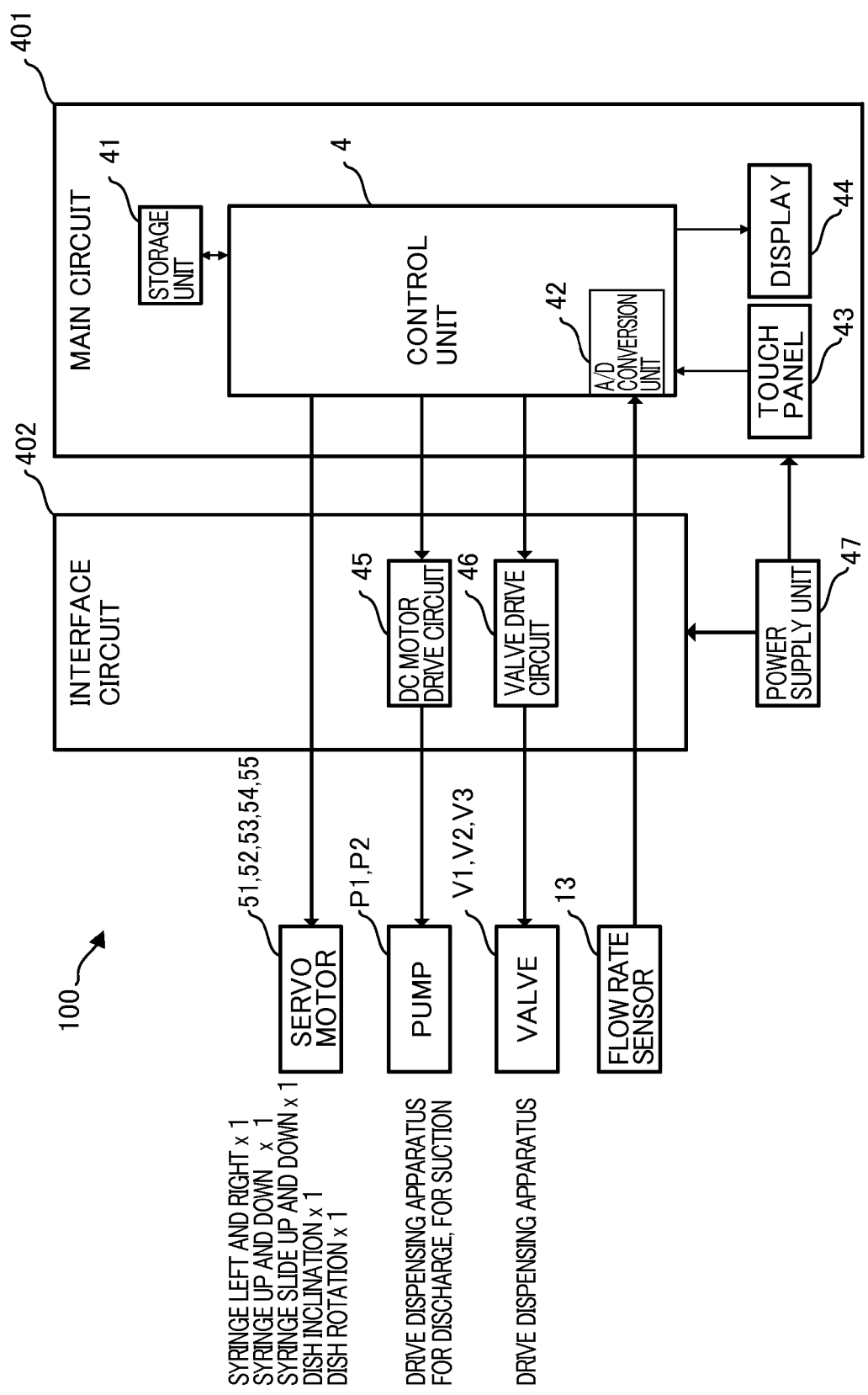
FIG. 3 is a block diagram illustrating a dispensing device according to an embodiment of the present disclosure.

Hereinafter, a main circuit and an interface circuit according to an embodiment of the present disclosure will be described with reference to FIG. 3. FIG. 3 is a block diagram illustrating the dispensing device according to an embodiment of the present disclosure.

The dispensing device 100 includes a main circuit 401 and an interface circuit 402.

The main circuit 401 is a circuit to control the dispensing device 100. A power supply voltage is supplied from a power supply unit 47 to the main circuit 401. The main circuit 401 includes the control unit 4, a storage unit 41 (first to sixth storage units), an A/D conversion unit 42, a touch panel 43, and a display 44.

The control unit 4 is a device to control the entire operation of the dispensing device 100. The control unit 4 is configured with, for example, a microcomputer capable of executing programs for controlling the dispensing device 100 which are stored in the storage unit 41.

The storage unit 41 stores programs to be executed by the control unit 4 and information which is referred to when the control unit 4 executes the programs. Note that the details of the information stored in the storage unit 41 will be described later.

The A/D conversion unit 42 cyclically converts a signal indicative of a detection result of the flow rate sensor 13 from analog signal to digital signal at sampling intervals of, for example, one millisecond. That is, a digital signal indicative of a detection result of the flow rate sensor 13 is outputted from the A/D conversion unit 42 every millisecond.

The touch panel 43 is a device used by an operator of the dispensing device 100 to input various instructions, such as operation start and operation stop instructions, to the dispensing device 100.

The display 44 is a device to output control states of the dispensing device 100, various alarms, and the like to the operator of the dispensing device 100.

The control unit 4 controls the servo motors 51 to 55, the pumps P1 and P2, and the valves V1 to V3 by executing programs stored in the storage unit 41.

The interface circuit 402 is a circuit to supply driving voltages to the pumps P1 and P2 and the valves V1 to V3. The interface circuit 402 includes a DC motor drive circuit 45 and a valve drive circuit 46.

The DC motor drive circuit 45 supplies driving voltages to the pumps P1 and P2 based on the control signals Sp1 and Sp2 outputted from the main circuit 401. Note that the driving voltages to be supplied to the pumps P1 and P2 will be described later.

The valve drive circuit 46 controls the opening and closing of the valves V1 to V3 based on the control signals Sv1 to Sv3 outputted from the main circuit 401. Note that, for example, when using solenoid valves as the valves V1 to V3, for example, opening and closing of the valves V1 to V3 are controlled by whether or not driving voltages are supplied to the solenoids of the valves V1 to V3. For example, when driving voltages are supplied to the solenoids of the valves V1 to V3, the valves V1 to V3 are assumed to be opened, and when the driving voltages are not supplied to the solenoids of the valves V1 to V3, the valves V1 to V3 are assumed to be closed. Note that, for the sake of convenience of explanation, hereinafter, description will be given of the case where solenoid valves are used for the valves V1 to V3.

—Control Unit—

Figure 4:
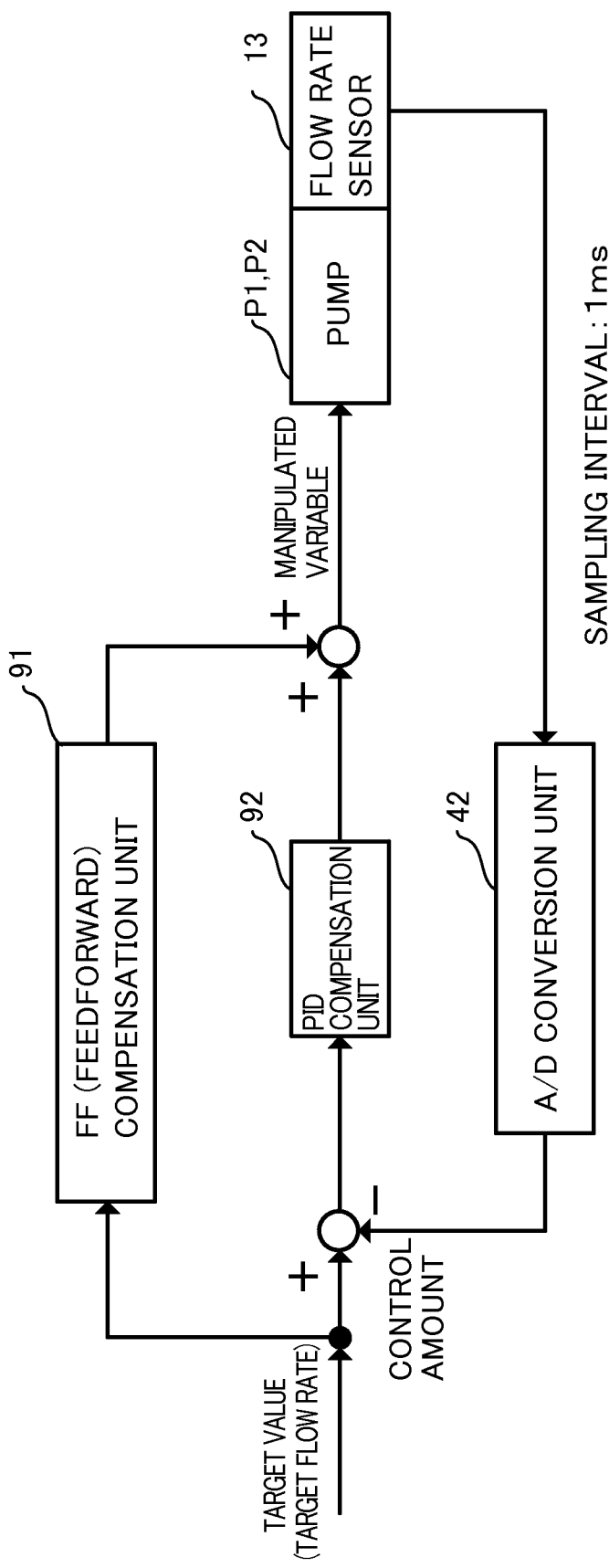
FIG. 4 is a block diagram illustrating control of a driving voltage for a pump performed by a control unit according to an embodiment of the present disclosure.

Hereinafter, a control unit according to an embodiment of the present disclosure will be described with reference to FIG. 4. FIG. 4 is a block diagram illustrating control of a driving voltage for a pump performed by the control unit according to an embodiment of the present disclosure. In the embodiment of the present disclosure, controlling the driving voltage is performed by PWM control of the driving voltage.

The control unit 4 performs control of the servo motors 51 to 55, flow rate control, and fluid volume control. Note that flow rate control indicates controlling the flow rate in the case of drawing liquid into the syringe 1 and that in the case of discharging the liquid in the syringe 1. Fluid volume control indicates controlling the volume of liquid to be drawn into the syringe 1 and the volume of the liquid in the syringe 1 to be discharged.

<Control of Servo Motors 51 to 55>

The control unit 4 controls the servo motors 51 to 55 so as to drive the syringe 1 and the dish mounting portion 22, for example, based on the programs stored in the storage unit 41.

<Flow Rate Control>

The control unit 4 controls the driving voltage (driving voltage for the pump P1) to be supplied to the pump P1 and the driving voltage (driving voltage for the pump P2) to be supplied to the pump P2.

The control unit 4 controls the driving voltage for the pump P1 so that the first flow rate, achieved by the pressure (negative pressure) generated at the pump P1, reaches a first target flow rate, when liquid is drawn into the syringe 1 through the nozzle 11. The control unit 4 controls the driving voltage for the pump P2 so that the second flow rate, achieved by the pressure generated by the pump P2, reaches a second target flow rate, when the liquid in the syringe 1 is discharged through the nozzle 11. The first target flow rate is a flow rate at which the liquid drawn in does not adhere to the filter 12 by the pressure generated by the pump P1 when the liquid has been drawn into the syringe 1 through the nozzle 11, for example. The second target flow rate is a flow rate at which the discharged liquid does not splatter around the dish 5 by the pressure generated by the pump P2 when liquid is discharged from inside the syringe 1 through the nozzle 11, for example. The first and second target flow rates are assumed to be acquired by, for example, experiments and the like.

The control unit 4 performs control of the driving voltage for the pump P1 at, for example, a cycle of five milliseconds. The control unit 4 includes a feedforward compensation unit 91 and a PID compensation unit 92. Note that the feedforward compensation unit 91 and the PID compensation unit 92 perform, for example, functions of the control unit 4 implemented by executing the programs stored in the storage unit 41. Note that the feedforward compensation unit 91 and the PID compensation unit 92 may be implemented, for example, as hardware. The PID compensation unit 92 starts controlling the driving voltage for the pump P1, after elapse of a predetermined time period since the feedforward compensation unit 91 has started controlling the driving voltage for the pump P1. Note that the predetermined time period is, for example, a time period from when the driving voltage for the pump P1 associated in advance with the first target flow rate is supplied to the pump P1 until when a steady state, where variations in the first flow rate are within a predetermined range, has been reached, and the predetermined time period is set, for example, at two hundred milliseconds.

<<Feedforward (FF) Compensation Unit 91>>

The feedforward compensation unit 91 controls the driving voltage for the pump P1 based on the driving voltage for the pump P1 associated in advance with the first target flow rate. Note that the driving voltage for the pump P1 associated in advance with the first target flow rate will be described later.

The control unit 4 controls the driving voltage for the pump P1, for example, based on the first target flow rate inputted from the touch panel 43 and an initial manipulated variable which is stored in the storage unit 41 in association with the first target flow rate. Note that the initial manipulated variable will be described later.

<<PID Compensation Unit 92>>

The PID compensation unit 92 feedback-controls the driving voltage for the pump P1 so that the calculated first flow rate reaches the first target flow rate. Note that the control unit 4 calculates the first flow rate based on a digital signal indicative of a detection result of the flow rate sensor 13 outputted from the A/D conversion unit 42, for example, every millisecond. The control unit 4 is assumed to calculate the first flow rate, for example, on the basis of a moving average of data 80 based on the digital signals which are continuously outputted from, for example, the A/D conversion unit 42 in order to prevent changes in the calculation result of the first flow rate caused by pulsation amplitude at the pump P1.

Note that since the control of the driving voltage for the pump P2 is similar to the control of the driving voltage for the pump P1, description thereof will be omitted.

<Fluid Volume Control>

The control unit 4 controls the start and stop of the pumps P1 and P2 and the valves V1 to V3.

The control unit 4 controls the start of the pumps P1 and P2, the stop of the pumps P1 and P2, and the opening and closing of the valves V1 to V3, based on the target fluid volume inputted, for example, from the touch panel 43 and the output from the A/D conversion unit 42. The control unit 4 integrates data which is based on the digital signals outputted from the A/D conversion unit 42, for example, every millisecond, and the result of such an integration is assumed to be the amount of the liquid sucked into the syringe 1 (hereinafter referred to as "suction volume of the liquid") or the amount of the liquid discharged from the syringe 1 (hereinafter referred to as "discharge volume of the liquid"). The control unit 4 determines whether or not the suction volume of the liquid has exceeded the target fluid volume and whether or not the discharge volume of the liquid has exceeded the target fluid volume. The control unit 4 controls the pumps P1 and P2 and the valves V1 to V3 based on the determination results.

For example, when drawing the liquid into the syringe 1, the control signal Sp1 for starting the pump P1, the control signal Sv1 for opening the valve V1, the control signal Sv2 for closing the valve V2, the control signal Sv3 for closing the valve V3 are outputted. For example, when it has been determined that the suction volume of the liquid has exceeded the target fluid volume while the liquid is being drawn into the syringe 1, the control unit 4 outputs the control signal Sv1 for closing the valve V1 and the control signal Sp1 for stopping the pump P1. For example, when discharging the liquid from the syringe 1, the control signal Sp2 for starting the pump P2, the control signal Sv1 for closing the valve V1, the control signal Sv2 for opening the valve V2, and the control signal Sv3 for closing the valve V3 are outputted. Here, the valve V3 is a valve to cause the liquid in the syringe 1 to flow out by free-fall (Hereinafter referred to as "free-fall discharge"), and to release the positive or negative pressure generated by the pump drive. The control of the valve V3 to be performed by the control unit 4 will be described later. For example, when it has been determined that the discharge volume of the liquid has exceeded the target fluid volume while the liquid is being discharged from the syringe 1, the control unit 4 outputs the control signal Sv2 for closing the valve V2 and the control signal Sp2 for stopping the pump P2.

—Correction of Initial Manipulated Variable (Calculation of Increase/Decrease Coefficient)—

Figure 8:
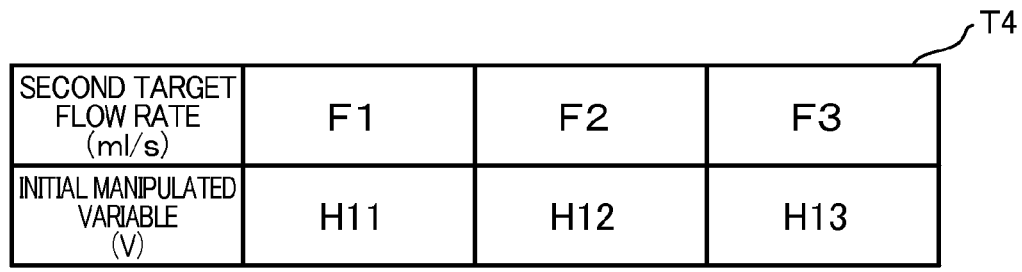
FIG. 8 is a diagram illustrating an initial manipulated variable of a second pump with respect to a second target flow rate when discharging liquid, in an embodiment of the present disclosure.
Figure 9:
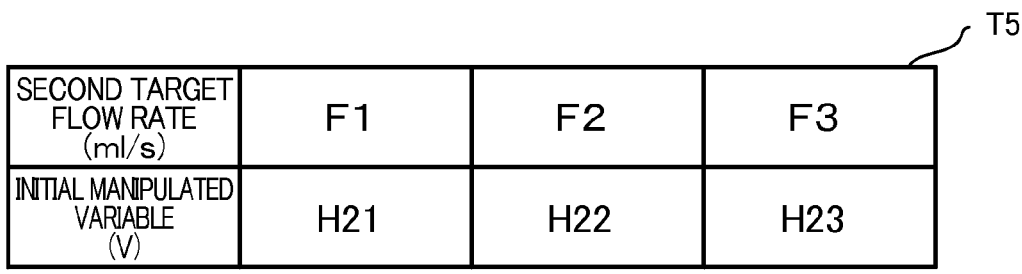
FIG. 9 is a diagram illustrating an initial manipulated variable of a second pump with respect to a second target flow rate when discharging air, in an embodiment of the present disclosure.
Figure 10:
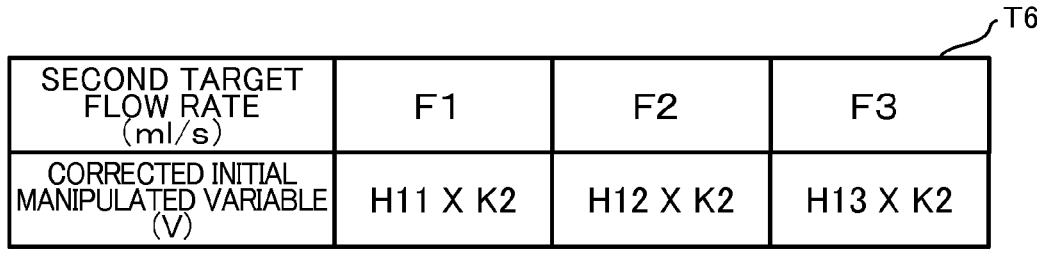
FIG. 10 is a diagram illustrating a corrected initial manipulated variable of a second pump with respect to a second target flow rate when discharging liquid, in an embodiment of the present disclosure.

Hereinafter, correction of an initial manipulated variable according to an embodiment of the present disclosure will be described with reference to FIG. 2, FIG. 3, and FIG. 5 to FIG. 10. FIG. 5 is a table illustrating initial manipulated variables of the first pump with respect to the first target flow rates when drawing in liquid, in an embodiment of the present disclosure. FIG. 6 is a table illustrating initial manipulated variables of the first pump with respect to the first target flow rates when drawing in air, in an embodiment of the present disclosure. FIG. 7 is a table illustrating corrected initial manipulated variables of the first pump with respect to the first target flow rates when drawing in liquid, in an embodiment of the present disclosure. FIG. 8 is a table illustrating initial manipulated variables of the second pump with respect to the second target flow rates when discharging liquid, in an embodiment of the present disclosure. FIG. 9 is a table illustrating initial manipulated variables of the second pump with respect to the second target flow rates when discharging air, in an embodiment of the present disclosure. FIG. 10 is a table illustrating corrected initial manipulated variables of the second pump with respect to the second target flow rates when discharging liquid, in an embodiment of the present disclosure.

The control unit 4 corrects the initial manipulated variables of the pumps P1 and P2 using liquid or air. Note that the configuration can be made to select between the control unit 4 correcting the initial manipulated variables of the pumps P1 and P2 using liquid or the control unit 4 correcting the initial manipulated variables of the pumps P1 and P2 using air, for example, based on an instruction inputted through the touch panel 43 by an operator or, for example, can be set in advance by the programs stored in the storage unit 41. Note that, the initial manipulated variable of the pump P1 is information indicative of the first driving voltage to be supplied to the pump P1 when the feedforward compensation unit 91 starts controlling the driving voltage for the pump P1. The initial manipulated variable of the pump P2 is similar to the initial manipulated variable of the pump P1.

Here, flag information Flag and tables T1 to T6 illustrated in FIG. 5 to FIG. 10 are stored in the storage unit 41.

The flag information Flag is information for selecting whether or not the initial manipulated variables of the pumps P1 and P2 are to be corrected by the control unit 4. For example, when the initial manipulated variables of the pumps P1 and P2 are to be corrected by the control unit 4, the flag information Flag is assumed to be set at "0". Whereas, for example, when the initial manipulated variables of the pumps P1 and P2 are not to be corrected by the control unit 4, the flag information Flag is assumed to be set at "1".

In table T1, a plurality of the first target flow rates F1 to F3 when drawing in liquid and a plurality of initial manipulated variables G11 to G13 of the pump P1 are respectively associated in advance with each other. In table T2, a plurality of the first target flow rates F1 to F3 when drawing in air and a plurality of initial manipulated variables G21 to G23 of the pump P1 are respectively associated in advance with each other. In table T3, a plurality of the first target flow rates F1 to F3 when drawing in a liquid and the corrected initial manipulated variables acquired by correcting the initial manipulated variables G11 to G13 given in table T1 are respectively associated with each other. In table T4, a plurality of the second target flow rates F1 to F3 when discharging liquid and a plurality of initial manipulated variables H11 to H13 of the pump P2 are respectively associated in advance with each other. In table T5, a plurality of second target flow rates F1 to F3 when discharging air and a plurality of the initial manipulated variables H21 to H23 of the pump P2 are respectively associated in advance with each other. In table T6, a plurality of the second target flow rates F1 to F3 when discharging liquid and the corrected initial manipulated variables acquired by correcting the initial manipulated variables H11 to H13 given in table T4 are respectively associated with each other.

Note that, here, the tables are configured such that the target flow rates in three stages and the initial manipulated variables thereof are associated with each other by way of example, but it is not limited thereto, and may be configured such that the target flow rates in greater multiple stages and the initial manipulated variables thereof are associated with each other.

<Configuration for Correcting Initial Manipulated Variable of Pump P1 Using Liquid>

The control unit 4 corrects the initial manipulated variable of the pump P1 by drawing a dispensing target (liquid) of the dispensing device 100 into the syringe 1. Note that it is preferable that the liquid to be used when correcting the initial manipulated variable of the pump P1 is a liquid having uniform density such as a culture medium or a reagent, for example. This is because there is a possibility that an increase/decrease coefficient, which will be described later, can not be acquired accurately when using a solution without a uniform viscosity and/or density in the process of sucking or discharging a solution having cells indifferent states mixed therein in cell culturing, for example. The control unit 4 acquires, from the table T1, the initial manipulated variable corresponding to the first target flow rate inputted from the touch panel 43, for example. The control unit 4 calculates an increase/decrease coefficient K1 indicative of the ratio (first ratio) of the manipulated variable when the first flow rate and the manipulated variable are stable with respect to the initial manipulated variable. Note that the manipulated variable when the first flow rate and the manipulated variable are stable is assumed to be the manipulated variable indicative of the driving voltage to be supplied to the pump P1 when, for example, the first flow rate reaches a flow rate corresponding to the first target flow rate and the fluctuation range of the first flow rate during a predetermined time period and the fluctuation range of the driving voltage to be supplied to the pump P1 become within a predetermined range of, for example, about one to two percents, under the aforementioned control of the driving voltages for the pump P1 performed by the feedforward compensation unit 91 and the PID compensation unit 92. The control unit 4 corrects the initial manipulated variable of the pump P1, by multiplying a plurality of the initial manipulated variables G11 to G13 of the pump P1 respectively associated in advance with a plurality of the first target flow rates F1 to F3 in table T1, by the increase/decrease coefficient K1. The corrected initial manipulated variables acquired by being corrected by the control unit 4 are respectively associated with the first target flow rates F1 to F3, and for example, are stored in table T3 of the storage unit 41.

<Configuration for Correcting Initial Manipulated Variable of Pump P2 Using Liquid>

The control unit 4 corrects the initial manipulated variable of the pump 2 by discharging liquid from the syringe 1. Note that the liquid to be used in correcting the initial manipulated variable of the pump P2 is assumed to be, for example, a liquid having uniform density. The control unit 4 acquires, from table T4, the initial manipulated variable corresponding to the second target flow rate inputted from the touch panel 43, for example. The control unit 4 calculates an increase/decrease coefficient K2 indicative of the ratio (second ratio) of the manipulated variable when the second flow rate and the manipulated variable are stable with respect to the initial manipulated variable. The control unit 4 corrects the initial manipulated variable of the pump P2, by multiplying a plurality of the initial manipulated variables H11 to H13 of the pump P2 respectively associated in advance with a plurality of the second target flow rates F1 to F3 in table T4, by the increase/decrease coefficient K2. The corrected initial manipulated variables acquired by being corrected by the control unit 4 are respectively associated with the second target flow rates F1 to F3, and for example, are stored in table T6 of the storage unit 41.

<Configuration for Correcting Initial Manipulated Variable of Pump P1 Using Air>

The control unit 4 corrects the initial manipulated variable of the pump P1 by drawing air into the syringe 1. The control unit 4 acquires, from table T2, the initial manipulated variable corresponding to the first target flow rate inputted from the touch panel 43, for example. The control unit 4 calculates the increase/decrease coefficient K1 indicative of the ratio (first ratio) of the manipulated variable when the first flow rate and the manipulated variable are stable with respect to the initial manipulated variable. The control unit 4 corrects the initial manipulated variable of the pump P1, by multiplying a plurality of the initial manipulated variables G11 to G13 of the pump P1 respectively associated in advance with a plurality of the first target flow rates F1 to F3 in table T1, by the increase/decrease coefficient K1. The corrected initial manipulated variables acquired by being corrected by the control unit 4 are respectively associated with the first target flow rates F1 to F3, and for example, are stored in table T3 of the storage unit 41.

<Configuration for Correcting Initial Manipulated Variable of Pump P2 Using Air>

The control unit 4 corrects the initial manipulated variable of the pump 2 by discharging the air from the syringe 1. The control unit 4 acquires, from table T5, the initial manipulated variable corresponding to the second target flow rate inputted from the touch panel 43, for example. The control unit 4 calculates the increase/decrease coefficient K2 indicative of the ratio (second ratio) of the manipulated variable when the second flow rate and the manipulated variable are stable with respect to the initial manipulated variable. The control unit 4 corrects the initial manipulated variable of the pump P2, by multiplying a plurality of the initial manipulated variables H11 to H13 of the pump P2 respectively associated in advance with a plurality of the second target flow rates F1 to F3 in table T4, by the increase/decrease coefficient K2. The corrected initial manipulated variables acquired by being corrected by the control unit 4 are respectively associated with the second target flow rates F1 to F3, and for example, are stored in table T6 of the storage unit 41.

—Discrimination of Maintenance Timing of Pumps P1 and P2—

Hereinafter, determination of timing for maintenance of the pumps P1 and P2 according to an embodiment of the present disclosure will be described with reference to FIG. 3.

The control unit 4 determines whether or not the increase/decrease coefficient K1 (first ratio) is equal to or greater than a first predetermined ratio and whether the increase/decrease coefficient K2 (second ratio) is equal to or greater than a second predetermined ratio. Note that the first predetermined ratio is assumed to be, for example, the ratio indicative of the timing for maintenance of the pump P1, and is set in advance for the pump P1. The second predetermined ratio is assumed to be, for example, the ratio indicative of the timing for maintenance of the pump P2, and is set in advance for the pump P2. When it has been determined that the increase/decrease coefficient K1 is equal to or greater than the first predetermined ratio, the control unit 4 is assumed to output a first signal indicating that the timing for maintenance of the pump P1. When it has been determined that the increase/decrease coefficient K2 is equal to or greater than the second predetermined ratio, the control unit 4 is assumed to output a second signal indicating that the timing for maintenance of the pump P2.

For example, when the first signal is outputted, a message indicating that the timing for maintenance of the pump P1 has come is assumed to be displayed on the display 44. For example, when the second signal is outputted, a message indicative of the timing for maintenance of the pump P2 is assumed to be displayed on the display 44.

—Operation of Dispensing Device—

Figure 11:
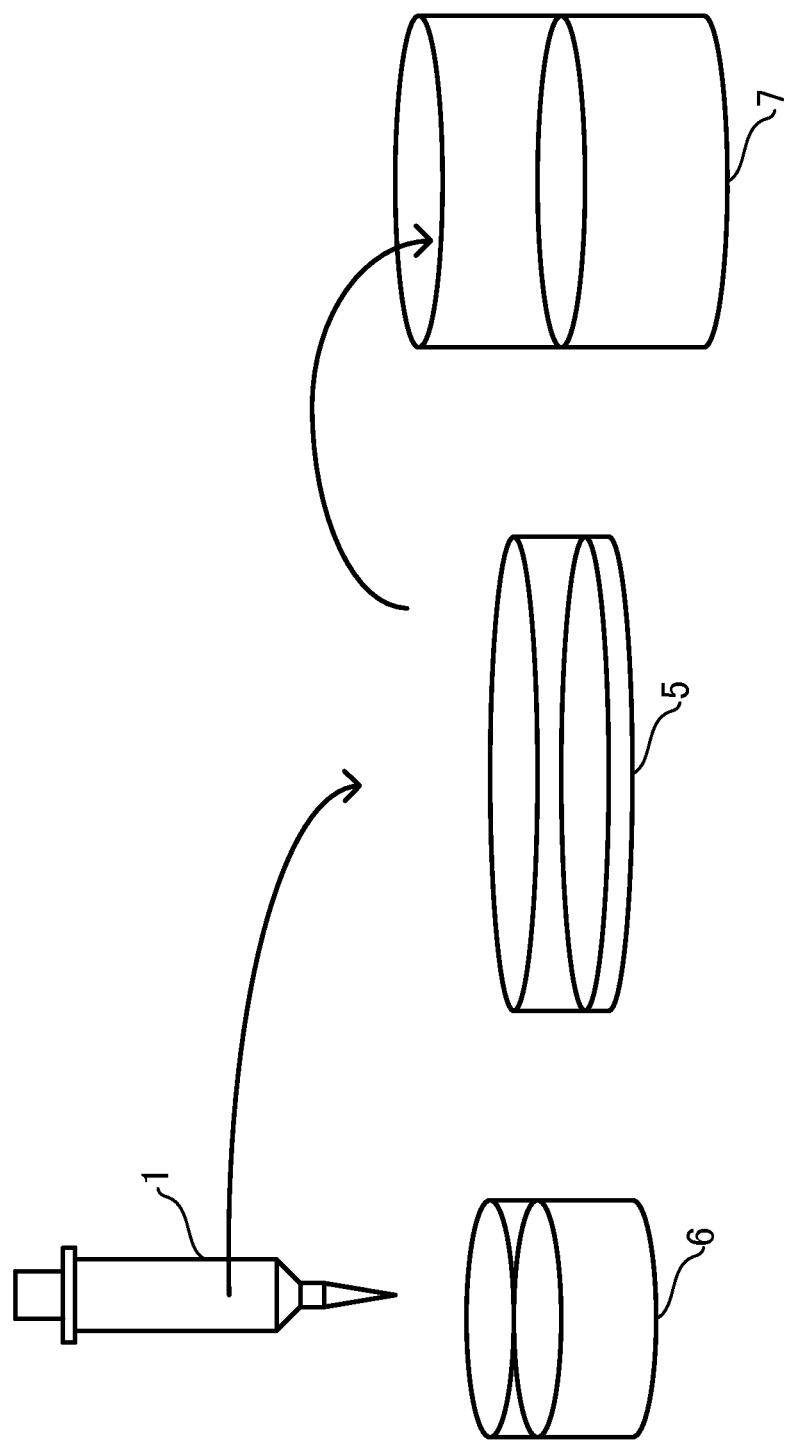
FIG. 11 is a diagram for explaining an example of an operation of a dispensing device according to an embodiment of the present disclosure.
Figure 12:
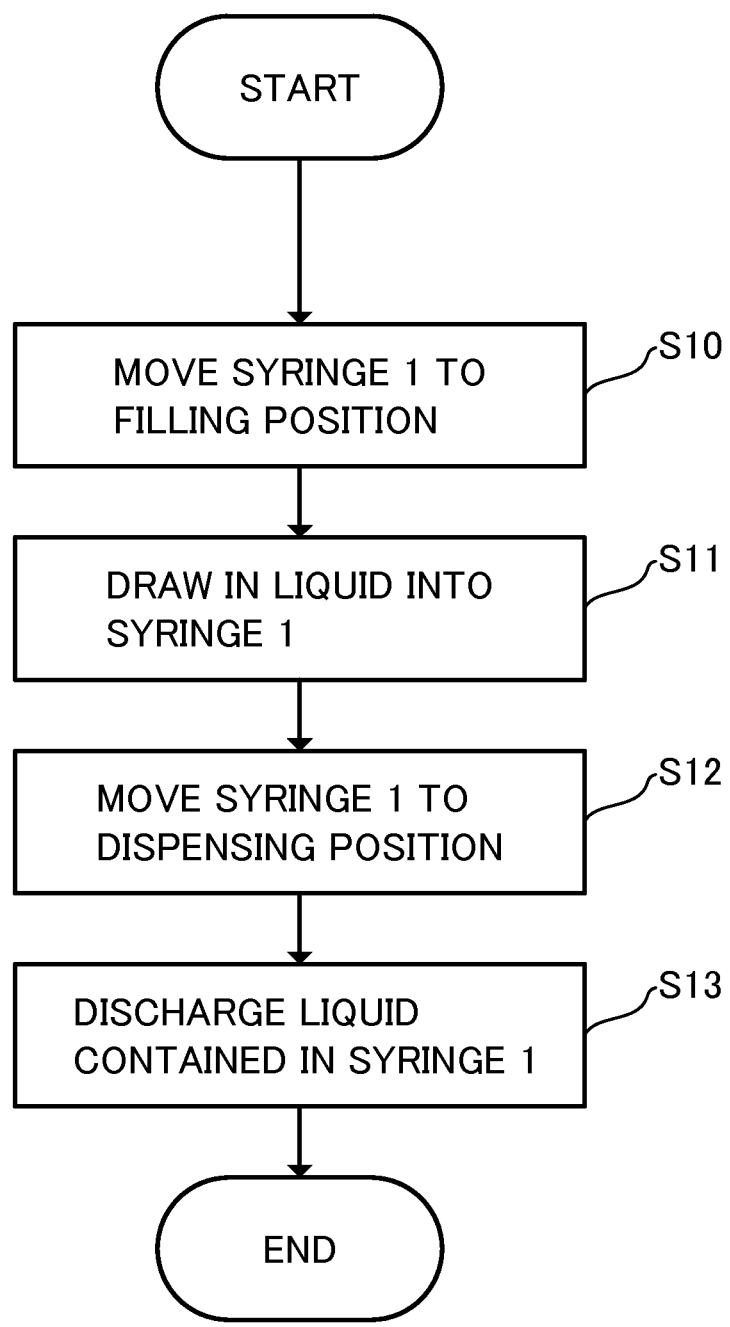
FIG. 12 is a flow chart illustrating an operation of a dispensing device according to an embodiment of the present disclosure.
Figure 13:
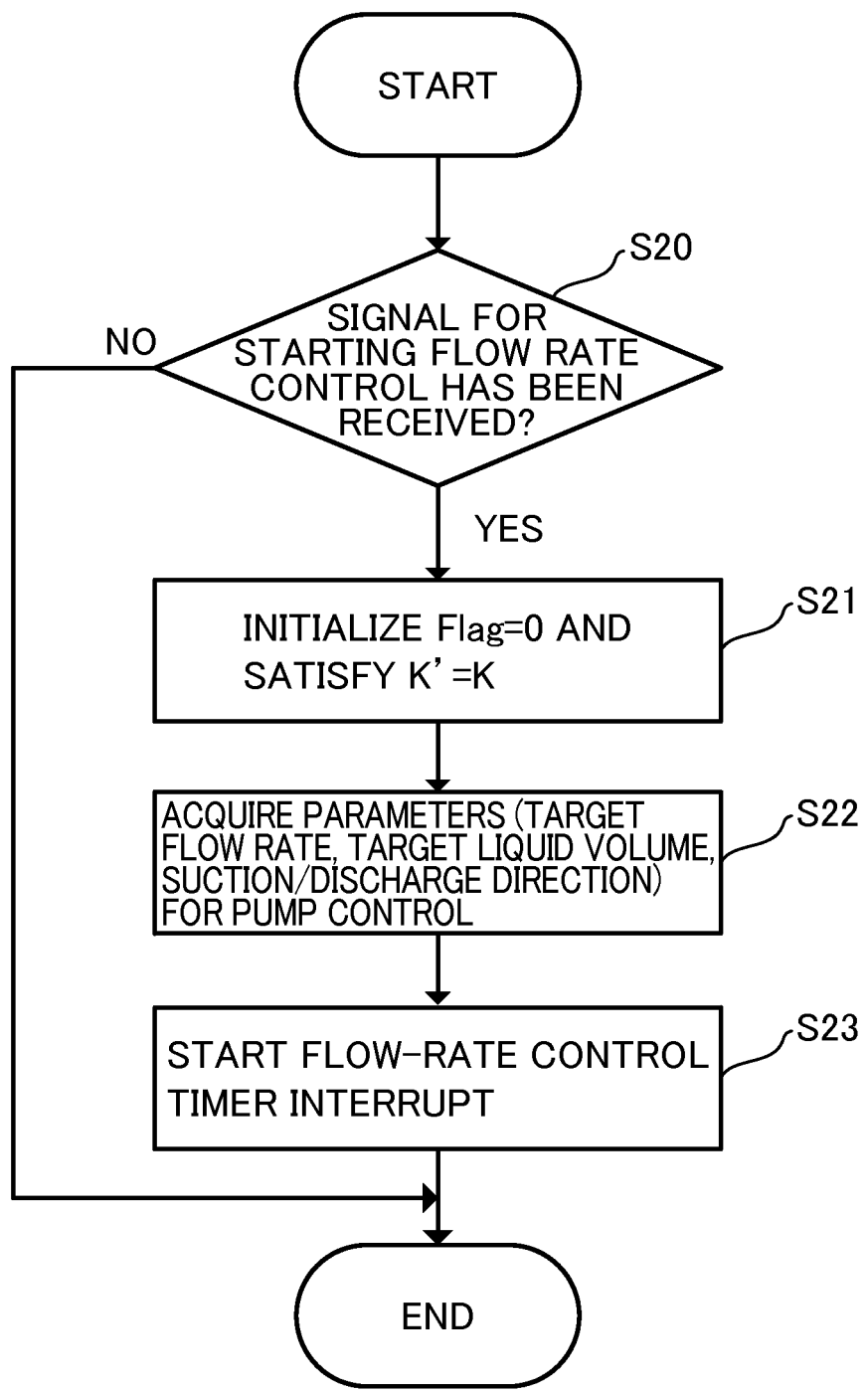
FIG. 13 is a flow chart illustrating an operation when starting flow rate control of a dispensing device according to an embodiment of the present disclosure.
Figure 14:
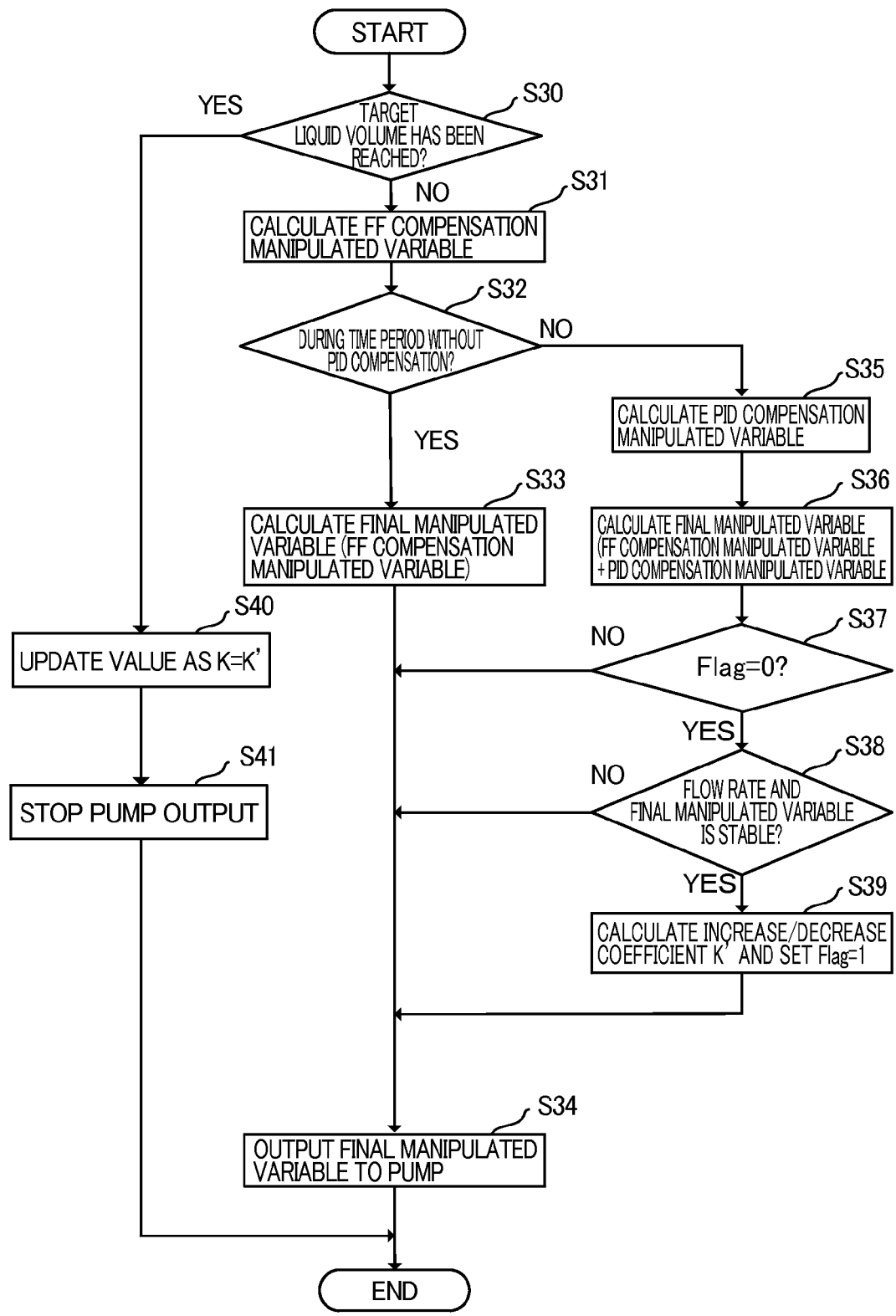
FIG. 14 is a flow chart illustrating an operation of flow rate control of a dispensing device according to an embodiment of the present disclosure.

Hereinafter, an operation of the dispensing device according to an embodiment of the present disclosure will be described with reference to FIG. 2 to FIG. 14. FIG. 11 is a diagram for explaining an example of an operation of the dispensing device according to an embodiment of the present disclosure. FIG. 12 is a flow chart illustrating an operation of the dispensing device according to an embodiment of the present disclosure. FIG. 13 is a flow chart illustrating an operation when starting flow rate control of the dispensing device according to an embodiment of the present disclosure. FIG. 14 is a flow chart illustrating an operation of flow rate control of the dispensing device according to an embodiment of the present disclosure.

The dispensing device 100, for example, draws into the syringe 1 liquid such as a culture medium for culturing cells stored in a reservoir 6 (FIG. 11) discharges the liquid contained in the syringe 1 to the dish 5, and thereafter, discharges the liquid remaining in the syringe 1 to a waste liquid tank 7. Note that the dispensing device 100 can also, for example, draw in liquid from the dish 5 and discharge the liquid to the reservoir 6, draw in liquid from the dish 5 and discharge the liquid to the dish 5, and draw in liquid from the reservoir 6 and discharge the liquid to the reservoir 6. Further, the dispensing device 100 can also, for example, draw in liquid from the reservoir 6 and discharge the liquid to the waste liquid tank 7.

For example, a description will be given of an operation of the dispensing device 100 and an operation of performing flow rate control of the dispensing device 100 when drawing the liquid stored in the reservoir 6 into the syringe 1, and discharging the liquid contained in the syringe 1 to the dish 5.

<Operation of Dispensing Device 100 (FIG. 12)>

A description will be given, for example, from where execution of programs stored in the storage unit 41 is started and the control unit 4 starts performing a control operation.

The control unit 4 controls the servo motors 51 to 53 so that the syringe 1 is moved to a position at which the liquid stored in the reservoir 6 can be drawn into the syringe 1 (step S10). The control unit 4 outputs the control signal Sp1 for starting the pump P1, the control signal Sv1 for opening the valve V1, the control signal Sv2 for closing the valve V2, and the control signal Sv3 for closing the valve V3, so that the liquid is drawn into the syringe 1. The DC motor drive circuit 45 supplies a driving voltage to the pump P1. Note that the pump P1 may be supplied with, for example, a predetermined fixed driving voltage or, for example, the driving voltage indicated by the corrected initial manipulated variables in table T3 (FIG. 7) corresponding to the first target flow rates, as the initial driving voltage.

The valve drive circuit 46 supplies a driving voltage only to the solenoid of the valve V1 among the valves V1 to V3. The valve V1 is opened, and the valves V2 and V3 are closed. The pump P1 generates a pressure for drawing liquid into the syringe 1. The liquid in the reservoir 6 is drawn into the syringe 1 (step S11). For example, when it has been determined that the suction volume of the liquid has exceeded the target fluid volume while liquid is being drawn into the syringe 1, the control unit 4 outputs the control signal Sv1 for closing the valve V1, and the control signal Sp1 for stopping the pump P1. In such a case, the valve V1 is closed and the pump P1 is stopped.

The control unit 4 controls the servo motors 51 to 53 so that the syringe 1 is moved to a position at which the liquid in the syringe 1 can be discharged to the dish 5 (step S12). The control unit 4 outputs the control signal Sp2 for starting the pump P2, the control signal Sv1 for closing the valve V1, the control signal Sv2 for opening the valve V2, and the control signal Sv3 for closing the valve V3, so that the liquid in the syringe 1 is discharged to the dish 5. The DC motor drive circuit 45 supplies the driving voltage to the pump P2. Note that the pump P2 may by supplied with, for example, a pre-determined fixed driving voltage or, for example, the driving voltage indicated in the corrected initial manipulated variables in table T6 (FIG. 10) corresponding to the second target flow rates, as the initial driving voltage.

The valve drive circuit 46 supplies the driving voltage only to a solenoid of the valve V2 among the valves V1 to V3. The valve V2 is opened, and the valves V1 and V3 are closed. A pump P2 generates pressure for discharging the liquid contained in the syringe 1. The liquid in the syringe 1 is discharged to the dish 5 (step S13). When it has been determined that the discharge volume of the liquid has exceeded the target fluid volume while the liquid in the syringe 1 is being discharged, the control unit 4 outputs the control signal Sv2 for closing the valve V2 and the control signal Sp2 for stopping the pump P2. In such a case, the valve V2 is closed and the pump P2 is stopped.

Note that, when the liquid in the syringe 1 is discharged to the dish 5, an operation may be performed such that the valve V2 is closed, the pump P2 is stopped, and the valve V3 is opened, after a part of the liquid in the syringe 1 is discharged by the pressure of the pump P2, as has been described. The liquid remaining in the syringe 1 flows out from the syringe 1 by free-fall under its own weight. In such a case, splattering and/or bubbling at the end of discharging the liquid can be suppressed, thereby being able to prevent contamination around the dish 5 caused by discharge of the liquid, for example.

Note that, for example, the control unit 4 may be configured to discriminate the timing for maintenance of the pumps P1 and P2 before or after the start of the operations in steps S11 and S13.

<Operation of Performing Flow Rate Control of Dispensing Device 100 (FIG. 13 and FIG. 14)>

A description will be given, for example, from where execution of programs stored in the storage unit 41 starts and the control unit 4 starts performing flow rate control.

The control unit 4 determines whether a signal for starting flow rate control has been received or not (step S20). Note that a configuration may be such that a signal for starting flow rate control is, for example, set in advance in a program in the storage unit 41 so as to be outputted to the control unit 4 when the operations in steps S11 and S13 are performed, and the signal can be, for example, inputted by an operator through the touch panel 43.

For example, when a signal for starting flow rate control is not received (NO in step S20), the control unit 4 ends the operation of performing flow rate control. On the other hand, for example, when a signal for starting flow rate control has been received (YES in step S20), the control unit 4 sets the flag information Flag to "0" to perform initialization, and substitutes an increase/decrease coefficient K for an increase/decrease coefficient K' (step S21). Note that the increase/decrease coefficient K is, for example, assumed to be stored in advance in the storage unit 41 as an initial value. The control unit 4 acquires target flow rates (first target flow rate, second target flow rate), a target fluid volume, and a suction/discharge direction, as parameters for controlling the pump P1 or P2 (step S22). Note that the suction or discharge direction is assumed to be a parameter for selecting between performing suction and performing discharge. Note that, for example, the first target flow rate F1, the predetermined target fluid volume, and the suction are assumed to be set through the touch panel 43, for example, as a target flow rate, a target fluid volume, a suction or discharge direction, respectively. The control unit 4 starts a flow-rate control timer interrupt (step S23). Note that the flow-rate control timer interrupt causes the control unit 4 to perform control of the pump P1 or P2, for example, with a cycle of five milliseconds.

The control unit 4 determines whether or not the suction volume of the liquid has reached the target fluid volume (has exceeded the target fluid volume) (step S30). For example, when it has been determined that the suction volume of the liquid has not reached the target fluid volume (NO in step S30), the control unit 4 calculates an FF (feedforward) compensation manipulated variable. The control unit 4, for example, acquires the initial manipulated variable G11 corresponding to the first target flow rate from table T1. The control unit 4 calculates the FF compensation manipulated variable by multiplying the initial manipulated variable G11 by the increase/decrease coefficient K (step S31). The control unit 4 determines whether or not it is during a time period without PID compensation (step S32). Note that the time period without PID compensation indicates a time period without control of the driving voltage for the pump P1 performed by the PID compensation unit 92, which is before a predetermined time has elapsed since the start of controlling the driving voltage for the pump P1 with the feedforward compensation unit 91. For example, when it has been determined that it is during a time period without PID compensation (YES in step S32), the control unit 4 calculates a final manipulated variable. The control unit 4 sets the FF compensation manipulated variable as the final manipulated variable (step S33). For example, the control unit 4 sets, as the final manipulated variable, the manipulated variable acquired by multiplying the initial manipulated variable G11 by the increase/decrease coefficient K. The control unit 4 outputs the control signal Sp1 so that the driving voltage indicated as the final manipulated variable is supplied to the pump P1. On this occasion, the DC motor drive circuit 45 supplies the driving voltage indicated as the final manipulated variable to the pump P1 (step S34). When it has been determined in the above step S32, for example, that it is not during the time period without PID compensation (NO in step S32), the control unit 4 calculates a PID compensation manipulated variable. The control unit 4 calculates the PID compensation manipulated variable, for example, according to the difference between the first target flow rate and the first flow rate (step S35). The control unit 4 calculates the final manipulated variable by adding the PID manipulated variable to the FF compensation manipulated variable calculated in the operation in step S31 (step S36). The control unit 4 determines whether the flag information Flag is set to "0" or not (step S37). For example, when it has been determined that the flag information Flag is not set to "0" (NO in step S37), the control unit 4 outputs the control signal Sp1 so that the driving voltage indicated as the final manipulated variable calculated in step S36 is supplied to the pump P1. On this occasion, the DC motor drive circuit supplies the driving voltage indicated as the final manipulated variable to the pump P1 (step S34). On the other hand, for example, when it has been determined that the flag information Flag is set to "0" (YES in step S37), the control unit 4 determines whether the first flow rate and the manipulated variable are stable or not, as has been described above (step S38). For example, when it has been determined that either the first flow rate or the manipulated variable is not stable (NO in step S38), the control unit 4 outputs the control signal Sp1 so that the driving voltage indicated as the final manipulated variable which has been calculated in step S36 is supplied to the pump P1. On this occasion, the DC motor drive circuit 45 supplies the driving voltage indicated as the final manipulated variable to the pump P1 (step S34). On the other hand, for example, when it has been determined that the first flow rate and the manipulated variable are stable (YES in step S38), the control unit 4 calculates the increase/decrease coefficient K', and sets the flag information Flag to "1" (step S39). Note that, for example, in the case where the flow rate control of the dispensing device 100 is performed when the operations in steps S11 and S13 are executed, and the liquid is drawn into the syringe 1, the control unit 4 acquires the initial manipulated variable corresponding to the first target flow rate F1 from table T1 (FIG. 5). The control unit 4 calculates, as the increase/decrease coefficient K', the increase/decrease coefficient K1, which is the ratio of the manipulated variable when the first flow rate and the manipulated variable are stable, with respect to the initial manipulated variable. Further, for example, in the case where the flow rate control of the dispensing device 100 is performed by an operator through the touch panel 43 and air is drawn into the syringe 1, the control unit 4 acquires the initial manipulated variable corresponding to the first target flow rate F1 from table T2 (FIG. 6). The control unit 4 calculates, as the increase/decrease coefficient K', the increase/decrease coefficient K1, which is the ratio of the manipulated variable when the first flow rate and the manipulated variable are stable, with respect to the initial manipulated variable. Note that, for example, the control unit 4 may correct the initial manipulated variable of the pump P1, by multiplying, by the coefficient K1, a plurality of the initial manipulated variables G11 to G13 of the pump P1 respectively associated in advance with a plurality of the first target flow rates F1 to F3 of table T1, and store the corrected initial manipulated variables in table T3 of the storage unit 41. The control unit 4 executes the operation in the aforementioned step S39, and thereafter, outputs the control signal Sp1 so that the driving voltage indicated as the final manipulated variable calculated in step S36 is supplied to the pump P1. On this occasion, the DC motor drive circuit 45 supplies the driving voltage indicated as the final manipulated variable to the pump P1 (step S34).

For example, when it has been determined that the suction volume of liquid has reached the target fluid volume in the determination in the aforementioned step S30 (YES in step S30), the control unit 4 substitutes the increase/decrease coefficient K' for the increase/decrease coefficient K, and updates the increase/decrease coefficient K (step S40). The control unit 4 outputs the control signal Sp1 for stopping the pump P1. On this occasion, the DC motor drive circuit 45 is brought into a state where the driving voltage is not supplied to the pump P1 (step S41). The pump P1 is stopped and, for example, the flow rate control performed by the control unit 4 is considered to end.

—Flow Rate of Liquid—

Figure 15:
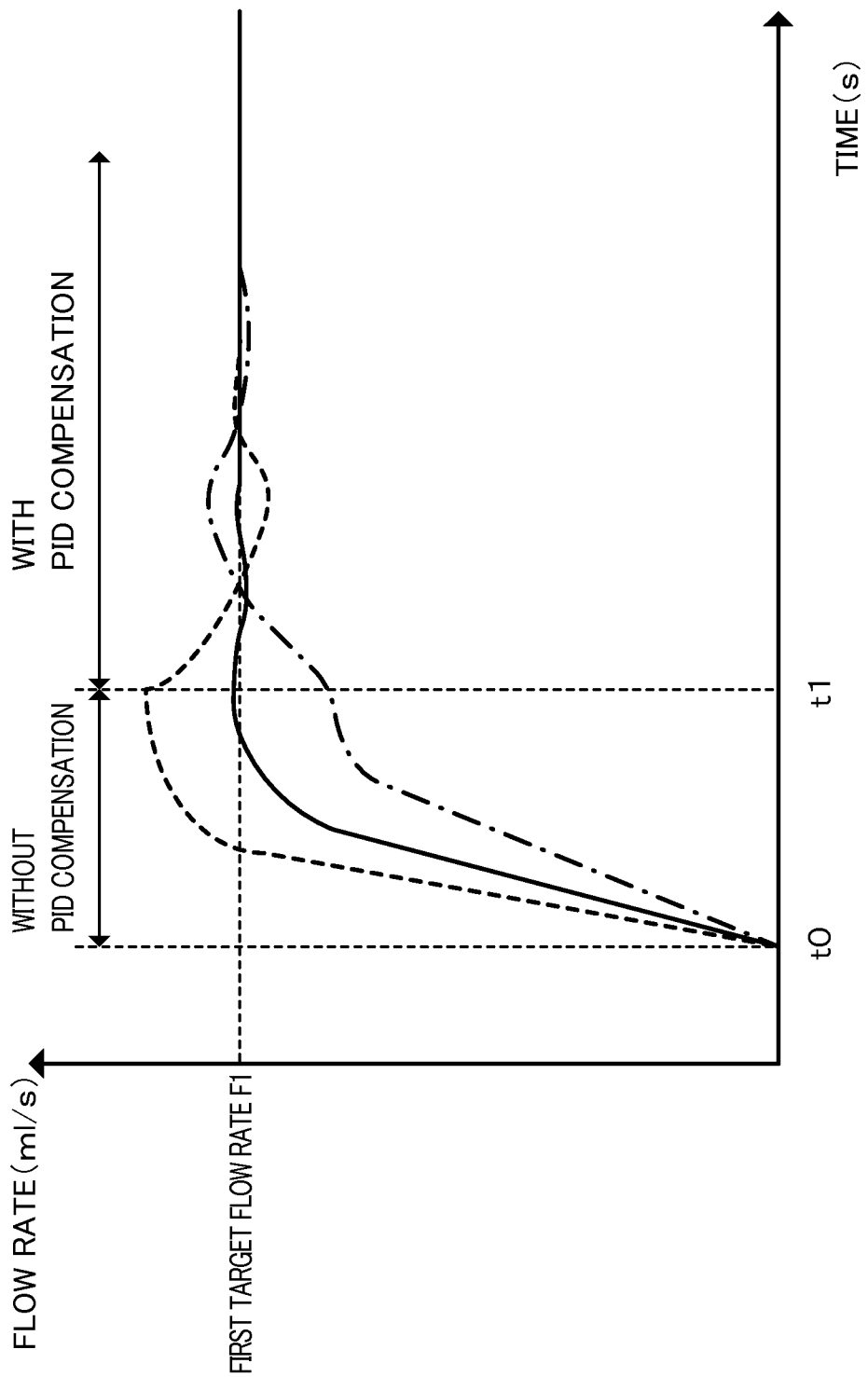
FIG. 15 is a characteristic diagram illustrating a relationship between a flow rate of a liquid and a time period elapsed since supply of a driving voltage to a pump for drawing in liquid according to an embodiment of the present disclosure.

Hereinafter, a flow rate of liquid according to an embodiment of the present disclosure will be described with reference to FIG. 15. FIG. 15 is a characteristic diagram illustrating a relationship between the flow rate of liquid and time period elapsed since the supply of driving voltage to the pump for drawing in liquid according to an embodiment of the present disclosure. The solid line in FIG. 15 indicates, for example, the flow rate of liquid drawn into the syringe 1, with respect to the time elapsed since the driving voltage indicated as the corrected initial manipulated variable corresponding to the first target flow rate F1 of the table T3 (FIG. 7) is supplied to the pump P1 (hereinafter referred to as, "when the present disclosure is applied"). The dotted line and the chain line in FIG. 15 indicates, for example, the flow rate of the liquid drawn into the syringe 1, with respect to the time elapsed since a voltage based on the driving voltage indicated as the initial manipulated variable G11 corresponding to the first target flow rate F1 of the table T1 (FIG. 5) is supplied to the pump P1 (hereinafter referred to as, "when the present disclosure is not applied"). Time t0 is assumed to be the time when the FF compensation unit 91 starts controlling the driving voltage for the pump P1. Time t1 is assumed to be the time when the PID compensation unit 92 starts controlling the driving voltage for the pump P1 after a predetermined time period has elapsed since the start of controlling the driving voltage for the pump P1 performed by the FF compensation unit 91.

When the present disclosure is applied, the flow rate of the liquid to be drawn into the syringe 1 reaches the first target flow rate, for example, between time t0 and t1, and a steady state is brought about in which variations in the flow rate are within a predetermined range, as indicated by the solid line.

On the other hand, when the present disclosure is not applied, the flow rate would vary for a time period until the flow rate enters the steady state, for example, during a time period from when the driving voltage is supplied to the pump P1 until when the flow rate of the liquid to be drawn into the syringe 1 reaches the first target flow rate to enter the steady state. For example, the flow rate of the liquid can not reach the first target flow rate only by the control of the driving voltage for the pump P1 performed by the FF compensation unit 91 (between the time t0 and the time t1), as indicated by the chain line, when the driving voltage indicated as the initial manipulated variable G11 is supplied to the pump P1, in the case where the pump P1 has deteriorated with time and/or a warm-up operation of operating the pump P1 under low load has not been performed for a predetermined time period. Further, for example, the flow rate of the liquid would exceed the first target flow rate, as indicated by the dotted line, if the warm-up operation of the pump P1 is performed for a longer time than expected, in the case where the level of the driving voltage to be supplied to the pump P1 is raised beyond the level of the driving voltage indicated as the initial manipulated variable G11 so that the flow rate of the liquid reaches the first target flow rate even with a short warm-up operation only by the control of the driving voltage for the pump P1 performed by the FF compensation unit 91.

As has been described, the dispensing device 100 can reliably correct a plurality of the driving voltages for the pump P1 corresponding to a plurality of target flow rates, so that the flow rate reaches the target flow rate, even in the case where the flow rate when drawing in liquid varies with the age deterioration of the pump P1 and/or the lengths of the warm-up operation of operating the pump P1 under low load, for example. Thus, the flow rate when drawing liquid into the syringe 1 can be made to reach the target flow rate. Further, for example, in the case where the flow rate varies with change in the friction between the liquid and the syringe 1 as well as the nozzle 11 due to the individual differences of the syringe 1 and the nozzle 11 which are accompanied by replacement of the syringe 1 and the nozzle 11, the flow rate when drawing liquid into the syringe 1 can be made to reach the target flow rate by correcting a plurality of driving voltages for the pump P1. Further, for example, in the case where the flow rate varies due to the wearing away of the surface that comes into in contact with the liquid in the syringe 1 or the nozzle 11 which is caused by repeated suction and discharge of a liquid, and/or by the accretions on the syringe 1 or the nozzle 11, the flow rate when drawing liquid into the syringe 1 can be made to reach the target flow rate by correcting a plurality of the driving voltages for the pump P1. Further, since the flow rate when drawing liquid into the syringe 1 can be made to reach the target flow rate, for example, liquid can be prevented from adhering to the filter 12, provided between the syringe 1 and the pump P1, due to the variations in the flow rate when drawing liquid into the syringe 1.

Further, the dispensing device 100 can reliably correct a plurality of the driving voltages for the pump P2 corresponding to a plurality of target flow rates, so that the flow rate reaches the target flow rate, even in the case where the flow rate when discharging liquid varies with, for example, the age deterioration of the pump P2 and/or the lengths or time of the warm-up operation of operating the pump P2 under low load. Thus, since the flow rate when discharging liquid can be made to reach the target flow rate, liquid splattering or the like around the dish 5 for dispensing liquid to contaminate the surroundings, for example, due to the variations in the flow rate when discharging a liquid from the syringe 1, can be prevented. Further, for example, time for drawing in or discharging a predetermined volume of liquid can be maintained constant. This in turn allows the quality of cells to be equalized.

Further, the storage unit 41 stores tables T1, T3, T4, and T6. The control unit 4 can correct the initial manipulated variables of the pumps P1 and P2 using a dispensing target (liquid) of the dispensing device 100. Thus, the driving voltages for the pumps P1 and P2 can be corrected using the same liquid as the dispensing target (liquid) of the dispensing device 100, thereby being able to improve the precision of the correction.

Thus, even in the case where age deterioration and/or change in flow rate along with warm-up operation occurs, a precise flow rate response as indicated by the solid line in FIG. 15 is enabled according to an embodiment of the present disclosure. Since the area surrounded by the curved line and the horizontal axis in FIG. 15 indicates the fluid volume to be discharged from the syringe, if the flow rate between time t0 and time t1 varies, time for discharging a predetermined volume would not be maintained constant. According to an embodiment of the present disclosure, time for drawing in or discharging a predetermined volume of a liquid can be maintained constant, as has been described above. This in turn allows the quality of cells to be equalized.

Further, the storage unit 41 stores tables T2 and T5 in addition to tables T1, T3, T4, and T6. The control unit 4 can correct the initial manipulated variables of the pumps P1 and P2 using air which is different from the dispensing target (liquid) of the dispensing device 100. Therefore, for example, the flow rate of the liquid can be set at the target flow rate starting from when liquid is drawn in or discharged for the first time, by correcting the initial manipulated variables of the pumps P1 and P2 using air prior to drawing in or discharging the liquid. Thus, for example, the liquid can be reliably prevented from adhering to the filter 12 provided between the syringe 1 and the pump P1 due to the variations in the flow rate when drawing liquid into the syringe 1. Further, for example, liquid splattering or the like around the dish 5 for dispensing liquid to contaminate the surroundings due to the variations in the flow rate when discharging a liquid from the syringe 1 can be reliably prevented.

Note that tables T3 and T6 are not necessarily required to be stored, and the initial manipulated variable corresponding to the target flow rate may be made to be calculated at any time.

Note that, the increase/decrease coefficients K1 and K2 acquired first after starting operation of the apparatus, or the increase/decrease coefficient acquired last may be stored in the storage unit 41, and then be read therefrom at the next start time to be used as the initial values of the increase/decrease coefficients K1 and K2. Here, the increase/decrease coefficients acquired first as described above may be used, when the operation of the apparatus is to finish in a relatively short time and the variations in the flow rate accompanied by warm-up operation have more effects than the variations in the flow rate caused by age deterioration. Further, the increase/decrease coefficient acquired last as described above may be read and used after starting the apparatus, when the operation of the apparatus lasts for a relatively long time and the variations in the flow rate caused by age deterioration have more effects than the variations in the flow rate accompanied by warm-up operation.

Further, a user of the dispensing device 100 can figure out the timing for maintenance of the pumps P1 and P2 from the outputs of the first and second signals. Thus, the pumps P1 and P2 can be replaced at maintenance timing, by determining the life of the pumps P1 and P2, for example, according to the degree of age deterioration and the like of the pumps P1 and P2. Therefore, the dispensing device 100 having superior maintainability can be provided.

Further, the flow rate sensor 13 is disposed on a part of the flow path where the flows join in a manner to be used by both the first flow path R1 and the second flow path R2. Thus, the first and the second flow rates are calculated based on a detection result of the single flow rate sensor 13, thereby being able to reliably correct the initial manipulated variables of both of the pumps P1 and P2. Therefore, both the flow rate when drawing liquid into the syringe 1 and the flow rate when discharging liquid contained in the syringe 1 can be made to reliably reach the target flow rates. Further, a configuration of the dispensing device 100 can be simplified, thereby being able to reduce the manufacturing cost of the dispensing device 100.

Note that the above embodiments of the present disclosure are simply for facilitating the understanding of the present disclosure and are not in any way to be construed as limiting the present disclosure. The present disclosure may variously be changed or altered without departing from its spirit and encompass equivalents thereof.

What is claimed is:

1. A dispensing device comprising:
   a syringe configured to draw in or discharge a fluid;
   a first pump configured to generate a pressure to draw the fluid into the syringe;
   a second pump configured to generate a pressure to discharge the fluid in the syringe;
   a flowmeter disposed on a flow path between the syringe and the first pump or the second pump; and
   a control circuit configured to correct a plurality of initial driving voltages for the first pump by:
   calculating a first ratio of, with respect to a driving voltage for the first pump associated in advance with a first target flow rate in a case where the syringe draws in a first fluid as the fluid, a driving voltage for the first pump when the flowmeter measures a flow rate corresponding to the first target flow rate in a case where the syringe draws in the first fluid, and
   multiplying, by the first ratio, the plurality of initial driving voltages for the first pump respectively associated in advance with a plurality of first target flow rates in a case where the syringe draws in a second fluid as the fluid.

2. The dispensing device according to claim 1, wherein:
   the control circuit is further configured to correct a plurality of initial driving voltages for the second pump by:
   calculating a second ratio of, with respect to a driving voltage for the second pump associated in advance with a second target flow rate in a case where the syringe discharges the first fluid, a driving voltage for the second pump when the flowmeter measures a flow rate corresponding to the second target flow rate in a case where the syringe discharges the first fluid, and
   multiplying, by the second ratio, the plurality of initial driving voltages for the second pump respectively associated in advance with a plurality of second target flow rates in a case where the syringe discharges the second fluid.

3. The dispensing device according to claim 2, further comprising: a storage for storing:
   information of the plurality of initial driving voltages for the first pump respectively associated in advance with the plurality of first target flow rates in the case where the syringe draws in the second fluid;
   corrected information of the plurality of initial driving voltages for the first pump;
   information of the plurality of initial driving voltages for the second pump respectively associated in advance with the plurality of second target flow rates in the case where the syringe discharges the second fluid; and
   corrected information of the plurality of initial driving voltages for the second pump, wherein
   the second fluid is a same fluid as the first fluid.

4. The dispensing device according to claim 2, further comprising: a storage for storing:
   information of the plurality of initial driving voltages for the first pump respectively associated in advance with the plurality of first target flow rates in the case where the syringe draws in the second fluid;
   corrected information of the plurality of initial driving voltages for the first pump;
   information of the plurality of initial driving voltages for the second pump respectively associated in advance with the plurality of second target flow rates in the case where the syringe discharges the second fluid;
   corrected information of the plurality of initial driving voltages for the second pump;
   information of the driving voltage for the first pump associated in advance with the first target flow rate in the case where the syringe draws in the first fluid; and
   information of the driving voltage for the second pump associated in advance with the second target flow rate in the case where the syringe discharges the first fluid, wherein:
   the second fluid is a fluid different from the first fluid,
   the control circuit is configured to correct the plurality of initial driving voltages for the first pump, by calculating the first ratio of, with respect to the driving voltage for the first pump that is information stored in the storage, the driving voltage for the first pump when the flowmeter measures the flow rate corresponding to the first target flow rate in the case where the syringe draws in the first fluid, and multiplying, by the first ratio, the plurality of initial driving voltages for the first pump that is information stored in the storage, and
   the control circuit is configured to correct the plurality of initial driving voltages for the second pump, by calculating the second ratio of, with respect to the driving voltage for the second pump that is information stored in the storage, the driving voltage for the second pump when the flowmeter measures the flow rate corresponding to the second target flow rate in the case where the syringe discharges the first fluid, and multiplying, by the second ratio, the plurality of initial driving voltages for the second pump that is information stored in the storage.

5. The dispensing device according to claim 2, wherein:
the control circuit is further configured to:
- determine whether or not the first ratio is equal to or greater than a first predetermined ratio set in advance with respect to the first pump;
- determine whether or not the second ratio is equal to or greater than a second predetermined ratio set in advance with respect to the second pump;
- output, when the first ratio is equal to or greater than the first predetermined ratio, a first signal indicative of timing for maintenance of the first pump; and
- output, when the second ratio is equal to or greater than the second predetermined ratio, a second signal indicative of timing for maintenance of the second pump.

6. The dispensing device according to claim 1, wherein:
the control circuit includes a microcomputer and a storage storing a program,
the program, when executed by the microcomputer, causes the control circuit to correct the plurality of initial driving voltages for the first pump.

* * * * *